United States Patent [19]
Ahern et al.

[11] Patent Number: 5,653,728
[45] Date of Patent: Aug. 5, 1997

[54] DISPOSABLE NON-LATEX TOURNIQUET

[75] Inventors: Brian F. Ahern, Ramsey; Hugh T. Conway, Verona; Kenneth R. Powell, Mahwah, all of N.J.

[73] Assignee: Becton, Dickinson and Company, Franklin Lakes, N.J.

[21] Appl. No.: 557,765

[22] Filed: Nov. 13, 1995

[51] Int. Cl.$^6$ .................................................. A61B 17/12
[52] U.S. Cl. .................................................. 606/203
[58] Field of Search ................................. 606/201–204

[56] References Cited

U.S. PATENT DOCUMENTS

| | | |
|---|---|---|
| 3,628,536 | 12/1971 | Glesne . |
| 3,910,280 | 10/1975 | Talonn . |
| 3,930,506 | 1/1976 | Overend .................. 606/203 |
| 4,273,130 | 6/1981 | Simpson . |
| 4,323,232 | 4/1982 | Terpening ................ 606/203 |
| 4,384,583 | 5/1983 | Speelman et al. . |
| 4,566,436 | 1/1986 | Loefqvist . |
| 4,661,099 | 4/1987 | von Bittera et al. . |
| 4,727,885 | 3/1988 | Ruff . |
| 4,737,885 | 4/1988 | Akutsu . |
| 4,807,753 | 2/1989 | Goldstein . |
| 4,870,978 | 10/1989 | Atwell . |
| 4,911,162 | 3/1990 | Wolff . |
| 5,015,251 | 5/1991 | Cherubini . |
| 5,074,873 | 12/1991 | Dioguardi . |
| 5,272,236 | 12/1993 | Lai et al. . |
| 5,278,272 | 1/1994 | Lai et al. . |

FOREIGN PATENT DOCUMENTS

WO94/13213  6/1994  WIPO ..................... A61B 17/12

*Primary Examiner*—William Lewis
*Attorney, Agent, or Firm*—Nanette S. Thomas

[57] ABSTRACT

A disposable non-latex tourniquet formed from a thermoplastic elastomer and an additive comprising slip and anti-block components. More particularly, the disposable non-latex tourniquet is formed from a metallocene octene based polymer and an additive comprising slip and anti-block components. The disposable non-latex of the present invention substantially minimizes discomfort to the patient and facilitates ease of use in knotting and releasing the tourniquet from the patient.

11 Claims, 3 Drawing Sheets

DISPOSABLE NON-LATEX TOURNIQUET

BACKGROUND OF THE INVENTION

1. Field of the Invention

This invention relates to a tourniquet and more particularly to a disposable non-latex tourniquet that minimizes slippage and discomfort to the patient and to facilitate ease of use in knotting and releasing the tourniquet. More particularly, the present invention relates to a disposable non-latex tourniquet for intravenous procedures and similar procedures for restricting venous blood flow to be used in lieu of conventional rubber or latex tourniquets. The disposable non-latex tourniquet of the present invention substantially minimizes discomfort to the patient and also reduces risk of transmission of infection to the patient, phlebotomist and other medical personnel.

2. Description of Related Art

A tourniquet is typically used to occlude a patient's vein and enable medical personnel to successfully perform a variety of intravenous procedures. These include, but are not limited to, routine medical procedures such as phlebotomy, intravenous catheter insertion, dialysis, blood transfusion, donation, intravenous therapy and infusion set insertion. Historically, tourniquets have been made from latex in various shapes, such as flat strips or tubing and approximately 18 inches in length. Latex tourniquets are commonly reused until they become visibly and unacceptably contaminated or lost.

Tourniquets are used in medical practice for example, when obtaining a blood sample. The medical technician or phlebotomist will normally place the tourniquet about the upper arm of the patient and apply pressure by tightening and slip knotting the tourniquet to induce swelling in the veins in the lower arm (to cause the veins to stand out). An appropriate venipuncture site is then selected and a needle inserted, the blood sample removed and the needle withdrawn. Thereafter, the tourniquet is removed usually by giving the tourniquet a quick pull to release the slip knot.

Drawbacks of existing latex tourniquets is that patients or phlebotomists may have allergic sensitivity to contact with latex. Also latex tourniquets may pinch the patient's skin and pull the body hair of the patient due to the low elastic modulus and the high recovery of the tourniquet latex material.

Therefore, it is desirable to produce an inexpensive, throw-away or disposable tourniquet which can be easily used and which would avoid problems experienced with existing latex tourniquets.

While the prior art discloses various tourniquet arrangements, some of them disposable, they are complicated designs which make them unsuitable for inexpensive manufacturing. In addition, many of the prior art tourniquets either have a surface which allows some slippage when positioned about the limb of a patient or a surface which will cause pinching or uncomfortable pulling of body hair or skin when used and some are inefficiently elastic. In addition, many of the prior art tourniquets are made of latex.

SUMMARY OF THE INVENTION

The present invention is a disposable non-latex tourniquet for restricting venous blood flow. The disposable non-latex tourniquet of the present invention desirably comprises a thermoplastic elastomer and an additive comprising slip and anti-block components.

Preferably, the thermoplastic elastomer includes, but is not limited to polyolefin blends, dynamically vulcanized blends, copolyesters, styrenics, styrenic/polyolefin blends, nylons, polyurethanes and metallocene polymers. Most preferably, the thermoplastic elastomer is a metallocene polymer.

Metallocene polymers are produced by single site catalyst technology and are available with a variety of comonomers including octene, butene and hexane. Most preferably, the metallocene polymer of the present invention is an octene based metallocene polymer. This particular metallocene polymer comprises about 15% to about 30% octene and most preferably about 24% octene. Octene based metallocene polymers exhibits excellent elastic properties, such as low modulus and high recovery.

Alternatively, the thermoplastic elastomer may be a metallocene based foam copolymer.

Preferably, the additive comprises slip and anti-block components.

Preferably, the additive comprises a slip component of an oil, wax or stearic acid. Most preferably the slip component is wax. The slip component is in the additive to provide the surface of the tourniquet with selected frictional characteristics so that the tourniquet will not slip when placed about the limb of a patient but released when the knot is released. In addition, the slip component substantially minimizes trauma to the patient by reducing the tendency of the tourniquet to pinch or pull body hair both when knotted and when released.

Preferably, the additive comprises an anti-block component of silica or carbon. Most preferably the anti-block component is silica. The anti-block component is in the additive to provide certain characteristics to the tourniquet including but not limited to allowing the metallocene polymer to be extruded into a film and wound into roll form without the film adhering to itself.

The disposable non-latex tourniquet of the present invention is most preferably formed as follows:

(a) cast extruding an octene based metallocene polymer and an additive into a film;

(b) master roll forming the film;

(c) unrolling the film; and (d) roll converting the film into disposable tourniquets.

The roll converting process comprises the following steps:

(a) perforating the film into tape like strips;

(b) slitting the film into tourniquet width size so that it may be wound onto individual cores;

(c) winding the tourniquets onto individual cores; and (d) packaging the wound cores into individual bags or boxes with means to allow the tourniquets to be separated individually.

Optionally, a message may be printed on the film after the perforating step.

Optionally, a corona treatment may be applied to the film after the cast extruding step and before the unrolled film is perforated.

Optionally, a lacquer coating may be applied to one or both sides of the film after the printing step.

The disposable non-latex tourniquet of the present invention consists of frictional characteristics so as to minimize slip when it is placed about the limb of a patient and which will also substantially minimize trauma to the patient by reducing the tendency of the tourniquet to pinch or pull body hair or skin when knotted and when released.

Primary advantages of the tourniquet of the present invention is that it is disposable, non-latex and more comfortable to the patient and is inexpensive to manufacture.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

Figure 1:
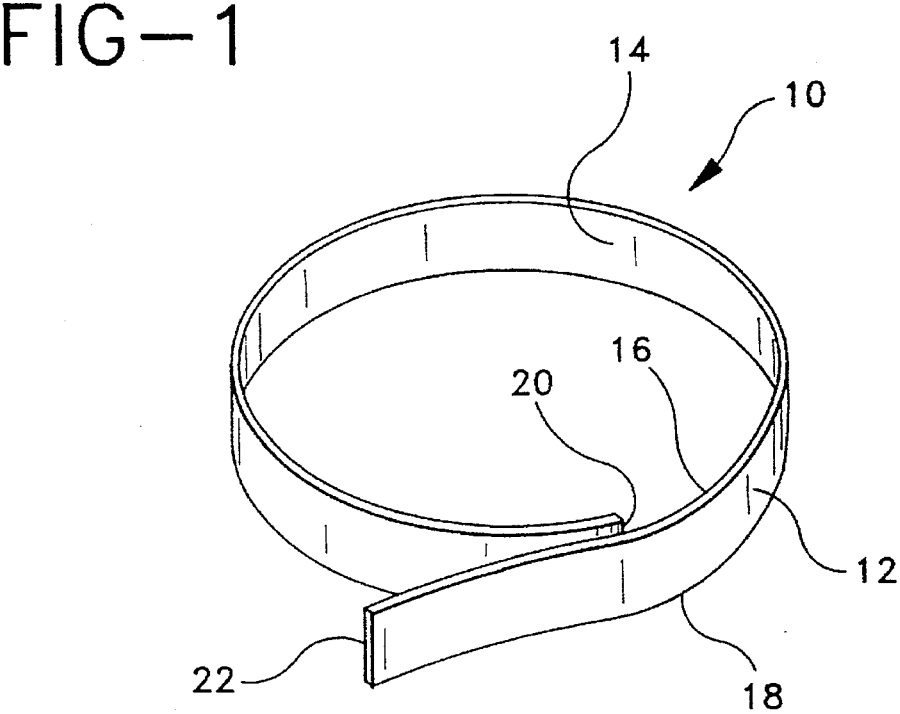
FIG. 1 is a perspective view of the disposable non-latex tourniquet of the present invention.

Referring to FIG. 1, the present invention is a disposable non-latex tourniquet 10 comprising an elongated strip of material comprising an upper surface 12, bottom surface 14, side edges 16 and 18 and opposite ends 20 and 22. The strip of material may be of various sizes, preferably about ¾" to about 1½" wide and about 12" to about 30" in length after cutting and finishing.

The disposable non-latex tourniquet comprises a thermoplastic elastomer and an additive comprising slip and antiblock components.

The thermoplastic elastomer preferably includes, but is not limited to nylon elastomers, polyurethane elastomers, polypropylene elastomers, styrenic elastomers, metallocene elastomers and polyolefin elastomers. Most preferably, the thermoplastic elastomer is a metallocene elastomer. Metallocene polymers are produced by single site catalyst technology and are available with a variety of comonomers including octene, butene and hexane. Most preferably, the metallocene polymer is an octene based metallocene polymer. This particular metallocene polymer comprises about 15% to about 30% octene and most preferably about 24% octene. Octene based metallocene polymers exhibit excellent elastic properties, such as low modulus and high recovery.

Alternatively, the thermoplastic elastomer may be a metallocene based foam copolymer.

Preferably, the additive comprises slip and anti-block components. Examples of slip components include, but are not limited to oils, wax and stearic acid. Most preferably the slip component is wax.

Examples of anti-block components include, but are not limited to silica or carbon. Most preferably the anti-block component is silica.

The slip component provides frictional characteristics to the disposable tourniquet and the anti-block component allows the metallocene polymer to be extruded into a film in roll form without the film adhering to itself.

Figure 2:
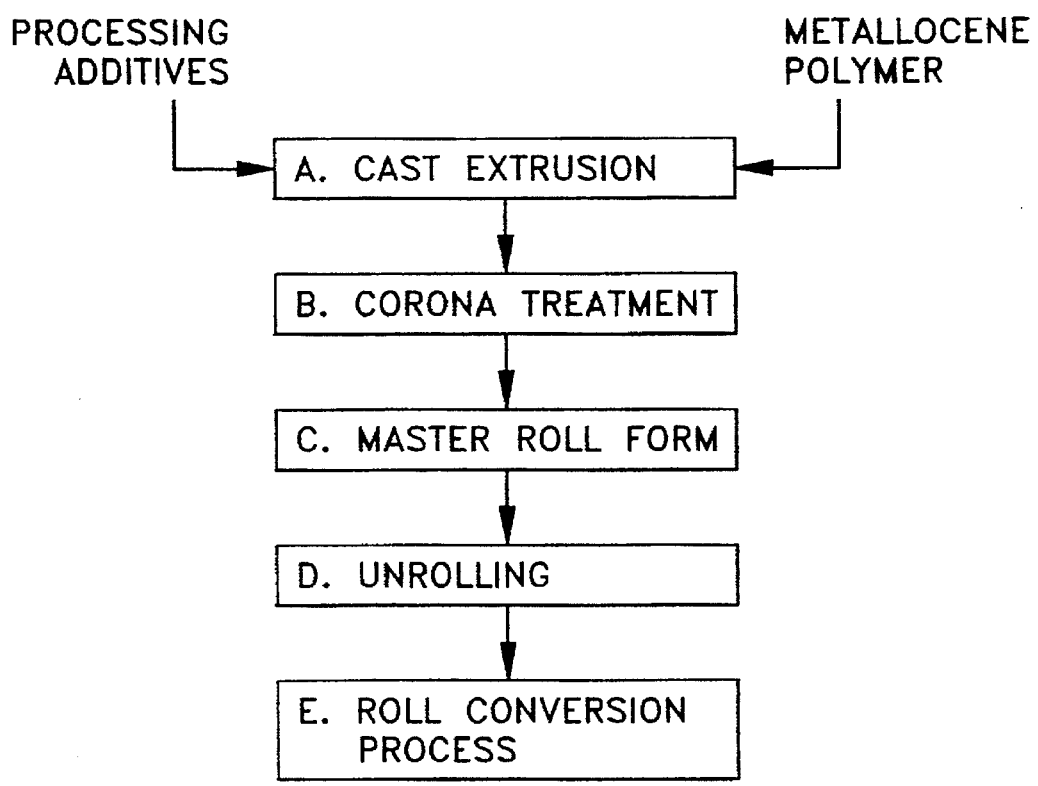
FIG. 2 is a schematic diagram of the steps in the method of manufacturing the disposable non-latex tourniquet of the present invention.

The method for making the disposable non-latex tourniquet of the present invention is schematically illustrated in FIG. 2.

As shown in FIG. 2, the first step of the manufacturing process is to convert the metallocene polymer and the additive into a film. This may be carried out by extrusion methods, such as blown or cast. Most preferably, the method of the present invention is carried out by cast extrusion A.

The film is then corona treated B and roll formed into a master roll form C. This step prepares the surface of the film for printing. The film is then unrolled D and processed through a roll conversion process E.

Figure 3:
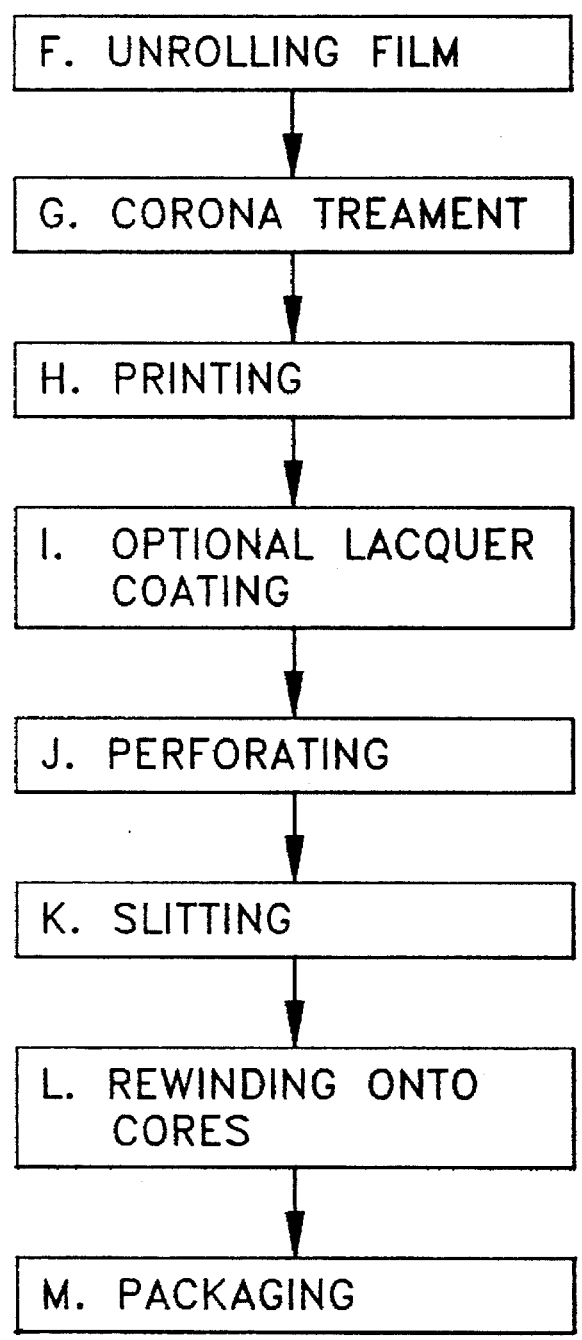
FIG. 3 is a schematic diagram of the steps in the roll conversion process in the method of manufacturing the disposable non-latex tourniquet of the present invention.

The roll conversion process E is schematically illustrated in FIG. 3. The roll conversion process first comprises unrolling the film F, followed by corona treatment G.

Then the film is provided with an imprinted message H. Most preferably appropriate messages may be imprinted on the tourniquet material which may be either in the form of advertising or include use instructions. Such imprinting may be carried out by offset, silk-screen or other printing techniques.

The corona treatment is used in the processing steps of the present invention to treat the film to allow ink to adhere to the surface of the film. Desirably, the corona treatment level is 40–46 dynes.

Then both sides of the film is coated with a lacquer material I. The lacquer overcoating will substantially prevent blocking of the individual tourniquets on the roll. This also substantially prevents the tourniquets from adhering to each other especially at high temperature.

The film is then perforated J. The perforations will allow for easy separation of the individual tourniquets.

The film is then serially slit K into tourniquet strips of various widths. The tourniquet strips may be cut using a die cutter. A die cutter may be a drum type cutter which has a plurality of circular cutting edges.

The tourniquets are then wound onto cores L. The cores are then either packaged M singly in a suitable manner such as in a poly bag or are rolled and contained in a box with a dispensing slot to allow the perforated tourniquet to be separated individually. The strips may also be rolled unperforate and contained in a box with a dispensing slot and cutter to facilitate withdrawing and severing a single tourniquet of variable length at the time of use.

The tourniquets of the present invention preferably are of a length of about 12 to about 30 and most preferably at about 18 inches. The width of the individual tourniquets is about ¾ inches to about 1½ inches and most preferably at about 1 inch. The thickness of the individual tourniquets is about 0.006 inches to about 0.024 inches and most preferably about 0.010–0.015±0.002 inches.

The disposable non-latex tourniquets of the present invention have a modulus of about 1000 to about 3000 PSI, a tensile strength of about 1000 to about 3000 PSI, an ultimate elongation of about 500 to about 1000% and are clear or semi-transparent.

Figure 4:
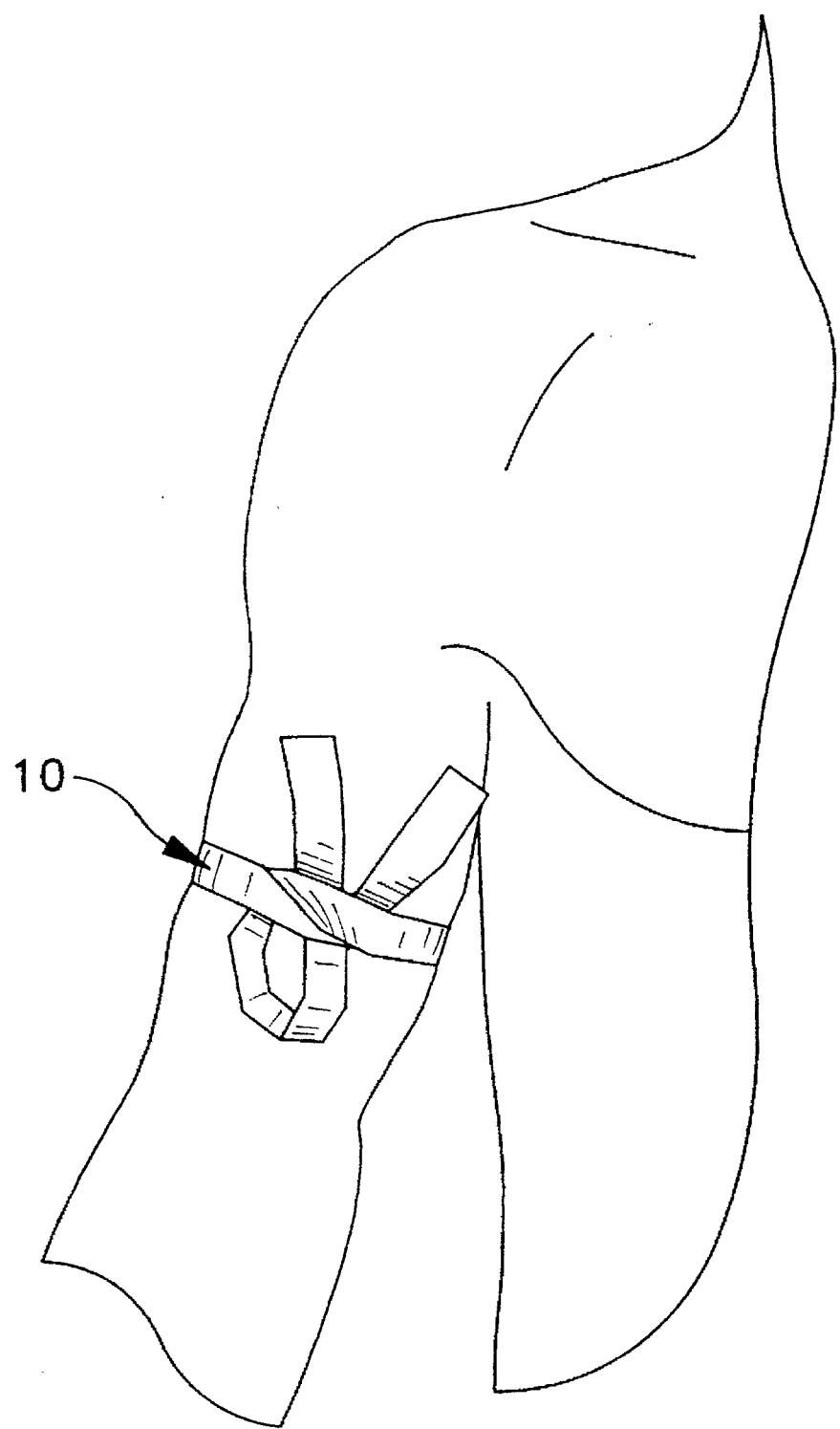
FIG. 4 illustrates the application of the disposable non-latex tourniquet to the arm of a patient.

In use, the disposable non-latex tourniquet of the present invention is placed about the limb of a patient and tightened by knotting as shown in FIG. 4. The knot is easily formed and stays in place without slipping. The knotting procedure does not pinch the patient or pull hair in a manner uncomfortable to the patient as is common with conventional latex tourniquets. After the phlebotomy procedure is initiated, the tourniquet is then easily released by pulling the knot to untie it.

Various other modifications will be apparent to an may be readily made by those skilled in the art without departing from the scope and spirit of the invention.

The example is not limited to any specific embodiment of the invention, but is only exemplary.

EXAMPLE

COMPARATIVE ANALYSIS OF THE NON-LATEX TOURNIQUET OF THE PRESENT INVENTION VERSUS A CONVENTIONAL LATEX TOURNIQUET

Physical testing was conducted on the non-latex tourniquet of the present invention and a conventional latex tourniquet. The results of the physical testing are reported in Table 1.

TABLE 1

|  | A | B |
|---|---|---|
| Length (inches) | 18 | 18 |
| Width (inches) | 1 | 1 |
| Thickness (mils) | 24 | 12 |
| Ultimate Tensile Strength Machine Direction (PSI) | 1730 | 1000 |
| Ultimate Elongation Machine Direction (%) | 855 | 700 ± 200 |
| 1% Secant Modulus Machine Direction (PSI) | 360 | 1500 ± 500 |
| Recovery After 30% Strain Machine Direction (PSI) | 98 | 93 |
| Recovery After 100% Strain Machine Direction (PSI) | 98 | 90 |

A = Vacutainer Brand Blood Collection Tourniquet, Reorder no. 7200 (Latex)
B = Disposable Non-Latex Tourniquet of the present invention Thus from the data it can be concluded that a disposable non-latex tourniquet has mechanical and physical properties similar to that of latex tourniquets.

What is claimed is:

1. A disposable non-latex tourniquet for restricting venous blood flow comprising an elongated strip of material comprising an upper surface, a bottom surface opposite side edges and opposite ends wherein said material comprises a thermoplastic elastomer and an additive comprising slip and anti-block components.

2. The tourniquet of claim 1 wherein said thermoplastic elastomer comprises polyolefins, styrenics, nylons, polyurethanes and metallocene polymers.

3. The tourniquet of claim 2 wherein said thermoplastic elastomer is a metallocene polymer.

4. The tourniquet of claim 3 wherein said metallocene polymer comprises a comonomer of octene, butene or hexane.

5. The tourniquet of claim 4 wherein said metallocene polymer comprises a comonomer of octene.

6. The tourniquet of claim 5 wherein said metallocene polymer comprises about 15% to about 30% octene.

7. The tourniquet of claim 6 wherein said metallocene polymer comprises about 24% octene.

8. The tourniquet of claim 1 wherein said slip component is an oil, was or stearic acid.

9. The tourniquet of claim 8 wherein said slip component is wax.

10. The tourniquet of claim 1 wherein said anti-block components is silica or carbon.

11. The tourniquet of claim 10 wherein said anti-block component is silica.

* * * * *